United States Patent [19]

Kelly

[11] Patent Number: 5,544,674
[45] Date of Patent: Aug. 13, 1996

[54] GAS MIXING APPARATUS FOR RESPIRATOR

[75] Inventor: Edmund F. Kelly, Murrieta, Calif.

[73] Assignee: Infrasonics, Inc., San Diego, Calif.

[21] Appl. No.: 502,629

[22] Filed: Jul. 14, 1995

[51] Int. Cl.[6] .................................................. G05D 11/03
[52] U.S. Cl. ............................ 137/98; 137/114; 137/607; 251/122
[58] Field of Search .............................. 137/98, 114, 607; 251/122

[56] References Cited

U.S. PATENT DOCUMENTS

| | | | |
|---|---|---|---|
| 2,616,710 | 11/1952 | Woodruff | 137/607 X |
| 3,116,748 | 1/1964 | Wasson | 137/607 X |
| 3,298,383 | 1/1967 | Cooper | 137/3 |
| 3,515,155 | 6/1970 | Haffner et al. | 137/7 |
| 3,534,753 | 10/1970 | Ollivier | 137/88 X |
| 3,633,576 | 1/1972 | Gorsuch | 128/145.8 |
| 3,669,134 | 6/1972 | Dobritz | 137/7 |
| 3,690,318 | 9/1972 | Gorsuch | 128/214 E |
| 3,871,371 | 3/1975 | Weigl | 128/145.8 |
| 3,889,669 | 6/1975 | Weigl | 128/145.8 |
| 3,903,881 | 9/1975 | Weigl | 128/145.6 |
| 4,022,234 | 5/1977 | Dobritz | 137/7 |
| 4,068,829 | 1/1978 | Laurent et al. | 137/607 X |
| 4,072,148 | 2/1978 | Munson et al. | 128/142.2 |
| 4,082,093 | 4/1978 | Fry et al. | 128/142.2 |
| 4,085,766 | 4/1978 | Weigl et al. | 137/88 |
| 4,141,356 | 2/1979 | Smargiassi | 128/145.8 |
| 4,177,830 | 12/1979 | Munson | 137/501 |
| 4,206,753 | 6/1980 | Fife | 128/201.21 |
| 4,237,925 | 12/1980 | Urushida | 137/607 X |
| 4,345,610 | 8/1982 | Herter et al. | 137/7 |
| 4,456,008 | 6/1984 | Clawson et al. | 128/205.19 |
| 4,687,013 | 8/1987 | Stevenson | 137/7 |
| 4,827,965 | 5/1989 | Wates | 137/114 X |
| 5,147,612 | 9/1992 | Raal | 422/99 |
| 5,244,118 | 9/1993 | Fallon et al. | 222/3 |

Primary Examiner—Stephen M. Hepperle
Attorney, Agent, or Firm—Brown, Martin, Haller & McClain

[57] ABSTRACT

A gas mixing valve has first and second inlet chambers linked to supplies of a first and second gas, and a mixing chamber having a blended gas outlet. The inlet chambers are connected to the mixing chamber via first and second control valves, each valve having a valve seat and valve member with opposing Surfaces defining a flow control orifice. Each valve seat and valve member are relatively movable between a closed position in which no flow occurs and a maximum opening position to define a series of orifices of progressively increasing area corresponding to the same geometrical progression. The position of each valve member can be controlled to provide a desired mixing ratio. Each valve seat is provided in a respective piston, and the pistons are tied together to move in response to variations in pressure drop across each piston, in order to vary the orifice size to compensate for changes in flow rate without changing the mixing ratio.

14 Claims, 4 Drawing Sheets

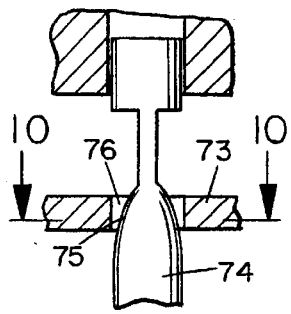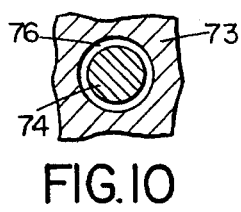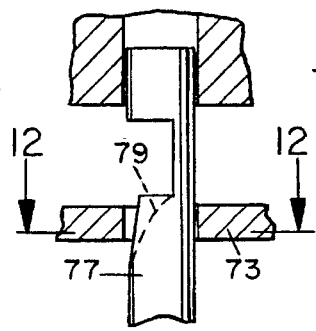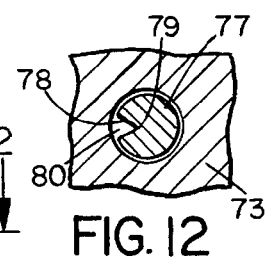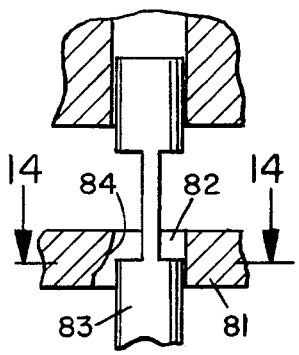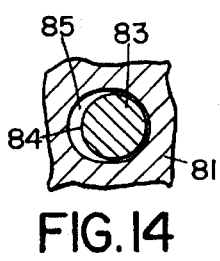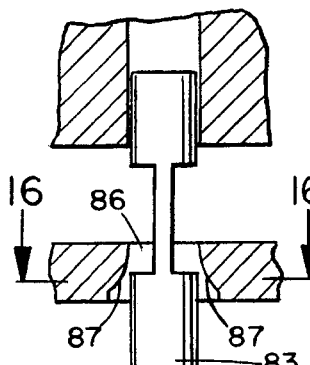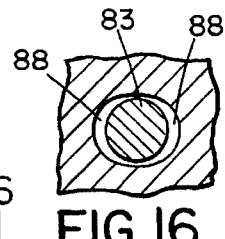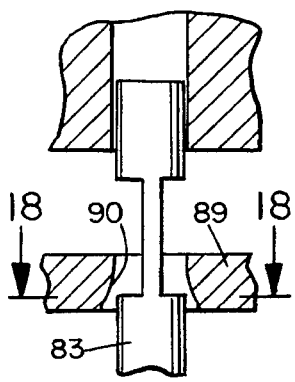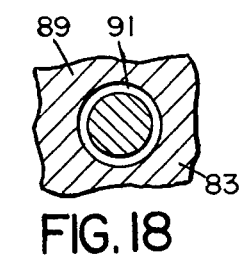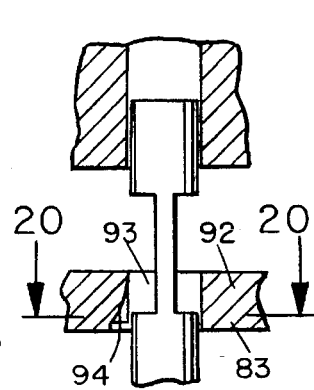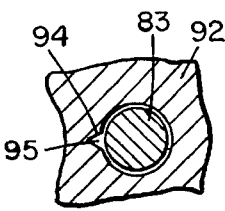

GAS MIXING APPARATUS FOR RESPIRATOR

BACKGROUND OF THE INVENTION

The present invention relates generally to gas mixing valves and methods for mixing together two or more gases in selected proportions, and is particularly concerned with a gas mixing valve or apparatus for use with a medical respirator in order to mix air and oxygen in a desired ratio.

Gas mixing valves are used to mix two or more different gases in desired proportions and to provide a desired output gas mixture. Such valves are used in medical respirators to mix air and oxygen to provide a suitable breathing mixture to a patient. Normally, a pair of poppet valve members are used to adjust the size of two orifices for controlling the proportions of the two different gases to be mixed. The size of the orifices is adjusted according to the desired mixture. One problem with such an arrangement is that mixing accuracy may be reduced as a result of reduction in the gas flow rates. Pressure drop across each valve will be proportional to the flow rate, and will increase as flow rate increases and decrease as the flow rate decreases. Generally, gas mixing valves have relatively good mixing accuracy at high flow rates, but significant errors in mixing accuracy can arise at low flow rates.

In the past, this problem has been dealt with by designing special mixing valves for low flow rate applications, which have smaller scale valves. This limits the range of flow rates over which any one mixing valve can operate effectively. Another solution is described in U.S. Pat. No. 4,072,148 of Munson et al., in which the mixing valve is provided with two stages. One, smaller valve stage is operated at all times, regardless of flow rate. The other, larger valve stage is operated only at high flow rates. Another alternative mixing valve arrangement is described in U.S. Pat. No. 4,085,766 of Weigl et al. In this apparatus, a piston is slidable in response to change in a reference gas pressure in order to adjust the size of two gas orifices in a sleeve surrounding the piston.

SUMMARY OF THE INVENTION

It is an object of the present invention to provide a new and improved gas mixing valve assembly in which relatively high mixing accuracy is provided regardless of gas flow rate, so that the mixing valve may be used for both high and low flow rates.

According to the present invention, a gas mixing valve assembly is provided which comprises an outer housing having a first inlet for a first gas, a second inlet for a second gas, and a blended gas outlet, the housing having a first gas chamber connected to the first inlet, a first piston slidably mounted in the first gas chamber, and having a first valve seat having a first orifice, a second gas chamber connected to the second inlet, a second piston slidably mounted in the second gas chamber and secured to the first piston so that the two pistons move together as a unit, the second piston having a second valve seat having a second orifice, a mixing chamber connected to the first and second chambers via the first and second piston orifices, respectively, a first valve member movably mounted in the housing for movement from a seated position against said first valve seat to close said first orifice away from said seated position to define an adjustable orifice of progressively increasing flow area as the valve member moves away from the valve seat, a second valve member movably mounted in the housing for movement from a seated position against said second valve seat to close said second orifice away from said valve seat to define an adjustable orifice of progressively increasing flow area as the valve member moves away from the seat, and a control member for controlling the positions of the first and second valve members to define a preselected ratio between the flow areas of the first and second orifices corresponding to a desired gas mixing ratio, and the opposing surfaces of each valve member and valve seat being of predetermined shape to define a series of progressive flow areas which correspond to a geometrical progression, the pistons being movable together in response to variations in pressure drop across the two valves to compensate for the pressure drop while maintaining substantially the same ratio between the first and second flow areas.

Thus, each valve is designed to have the same geometrical progression in flow area from the maximum orifice opening down to the minimum opening. The shape of the valve member or the valve seat, or both, is designed such that the desired geometrical progression is achieved. This is done by first determining the maximum orifice opening or flow area and the length of valve member travel away from the closed position to reach the maximum orifice opening. The valve movement is then divided into increments, with each increment of valve movement corresponding to a term of the progression. An orifice opening area is calculated for each increment of valve opening according to the progression ratio, and the valve member or valve seat is shaped in order to achieve the calculated areas for each step of valve movement in the progression. In this way, the ratio between the two orifices will be maintained regardless of the piston position. In other words, if each valve has an orifice area which increases by the same amount for each increment of valve or valve seat movement, regardless of the initial position of the valve or valve seat, once the mixing ratio has been set, movement of both valve seats by the same distance or number of increments will not change the mixing ratio.

In one embodiment of the invention, each orifice is cylindrical or circular and each valve member comprises a generally cylindrical poppet having a radius substantially equal to that of the orifice, with opposing wedge-shaped, curved cut-out surfaces on opposite sides of the poppet which define a pair of semi-cylindrical openings of gradually increasing area between respective cut-out surfaces and the opposing surface of the opening. This shape is particularly convenient for obtaining a geometrical progressive orifice area, since a large change in radius will produce a relatively small change in orifice area, making the cut-out surfaces relatively easy to machine with sufficient accuracy.

In alternative embodiments, the poppet valve may have a wedge-shaped cut-out defining a single semi-cylindrical opening. Alternatively, the poppet valve may be cylindrical while the wedge-shaped cut-outs are provided in opposing regions of the opening in the piston. Alternatively, the poppet valve or valve seat may be of conical shape to define the desired progression, or the poppet valve or valve seat may have an appropriately shaped cut-out or slot to define a triangular orifice of gradually increasing size as the valve and valve seat move apart.

In this way, a mixing valve can be provided which provides accurate mixing at both high and low flow rates. If the flow rate decreases, the pistons will move towards the valve members, reducing the size of each orifice while maintaining the same ratio between the two orifice flow areas. Thus, the passageway or orifice area for each of the two gases is increased or decreased automatically with changes in flow rate, with the percentage increase or decrease being the same in both valves so that the mixing proportions are maintained. This enables the blender or mixing apparatus to act as both a high flow and low flow blender while maintaining blending accuracy. Although the gas mixing apparatus or valve of this invention is primarily for use in a respirator, it will be understood that it may alternatively be used in other applications where controlled mixing of gases is required.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which:

FIG. 9 is a view similar to FIG. 7, showing a conical-type poppet;

FIG. 10 is a sectional view taken on line 10—10 of FIG. 9;

FIG. 11 is a view similar to FIG. 7, showing a V-groove poppet configuration;

FIG. 12 is a sectional view taken on line 12—12 of FIG. 11;

FIGS. 13–20 correspond to FIGS. 7–12, but with the different variable opening configurations incorporated in the valve seat openings instead of on the poppets;

DESCRIPTION OF THE PREFERRED EMBODIMENT

Figure 1:
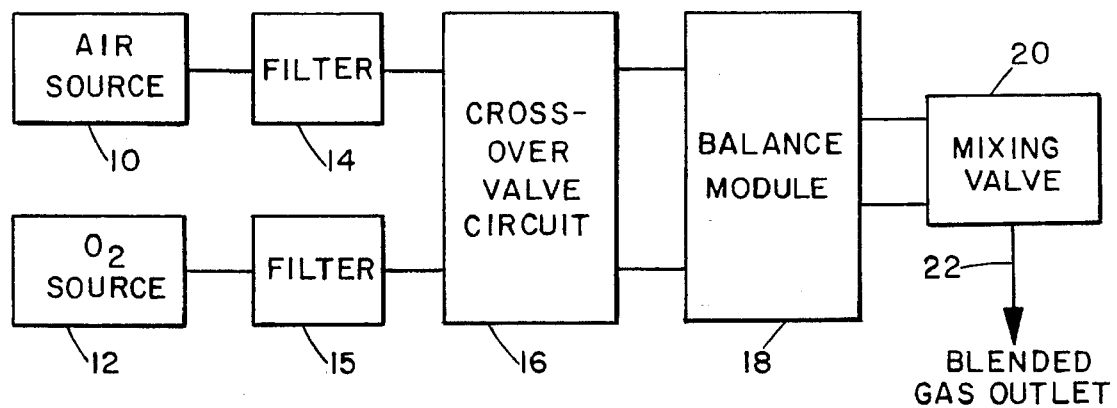
FIG. 1 is a block diagram of a typical gas mixing system or respirator.

FIG. 1 of the drawings schematically illustrates a typical gas blending system or respirator comprising a source of air 10 and a source of oxygen 12 each connected via a filter 14,15, respectively, to a cross-over valve circuit 16. The air and oxygen outputs of circuit 16 are connected to a balance module 18, and the outputs of module 18 are connected to a mixing valve 20 which mixes the gases according to the selected proportions and provides a blended gas output 22. The blender mixes air and oxygen to provide a pressurized gas source that ranges from 21% to 100% in oxygen concentration. Filters 14 and 15 are typically 5 micron filters. The filtered gases pass through the cross-over valve/alarm circuit which is designed to cause an alarm if inlet pressure of either gas drops below a predetermined level.

Balance module 18 is designed to equalize the operating pressure of the gas sources before entering the mixing valve 20. The cross-over valve and balance module will both be of a conventional nature and are therefore not described in any more detail.

Figure 2:
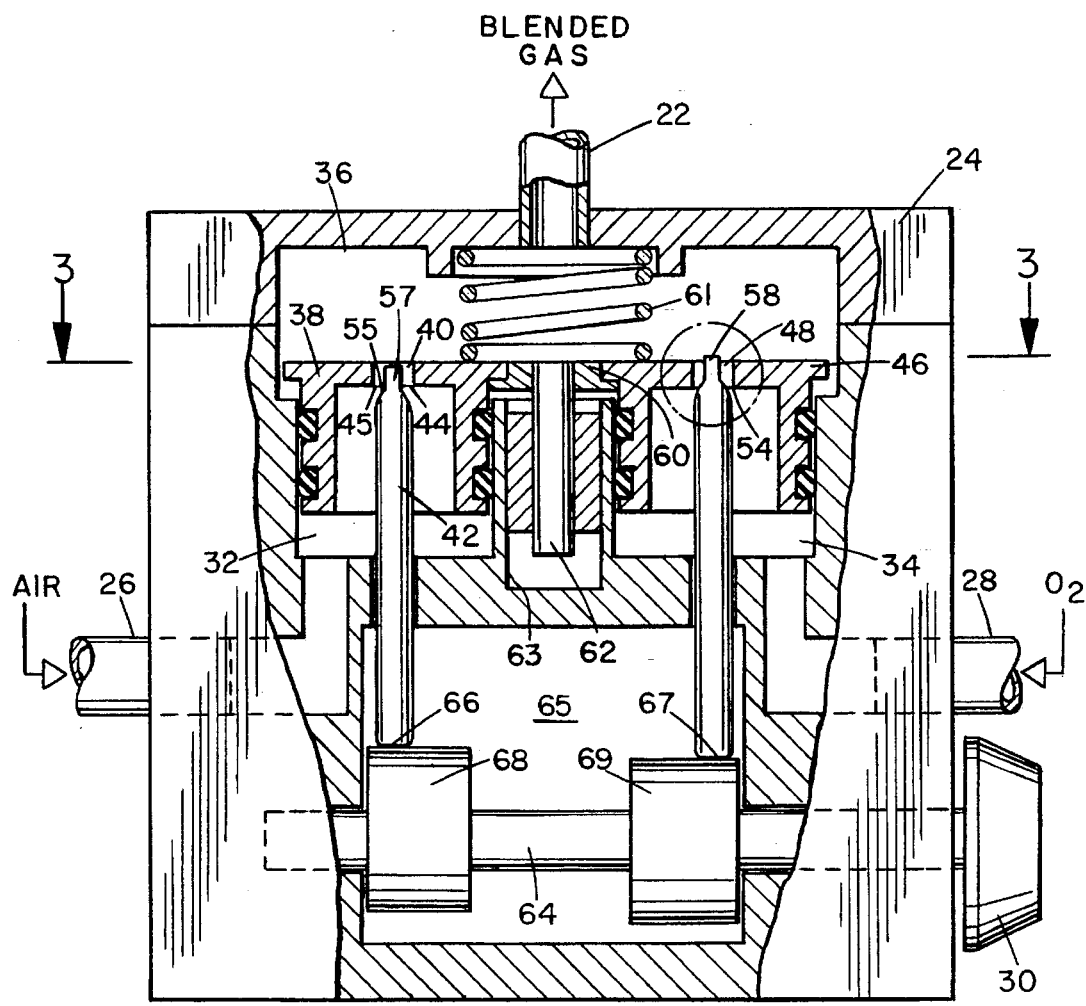
FIG. 2 is a side elevation view, partially cut away, of a mixing valve for a gas mixing system according to a preferred embodiment of the invention.

FIG. 2 of the drawings illustrates a mixing valve according to a first embodiment of the present invention for use in the mixing system or gas blender of FIG. 1. The mixing valve is designed to control the proportions of the two gases provided at blended gas output 22. The mixing valve basically comprises a housing 24 having an inlet 26 for air or a first gas, a second inlet 28 for oxygen or a second gas, and blended gas output 22. A control knob 30 is provided for controlling the proportions of air and oxygen in the blended gas output provided to a patient. The housing has a first chamber 32 connected to first inlet 26, a second chamber 34 connected to second inlet 28, and a mixing chamber 36 connected to outlet 22.

Figure 4:
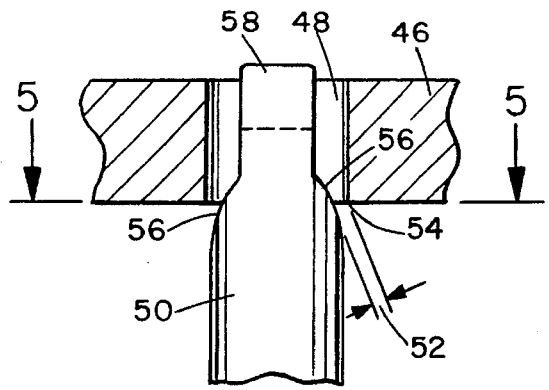
FIG. 4 is an enlarged sectional view taken on line 4—4 of FIG. 3.
Figure 5:
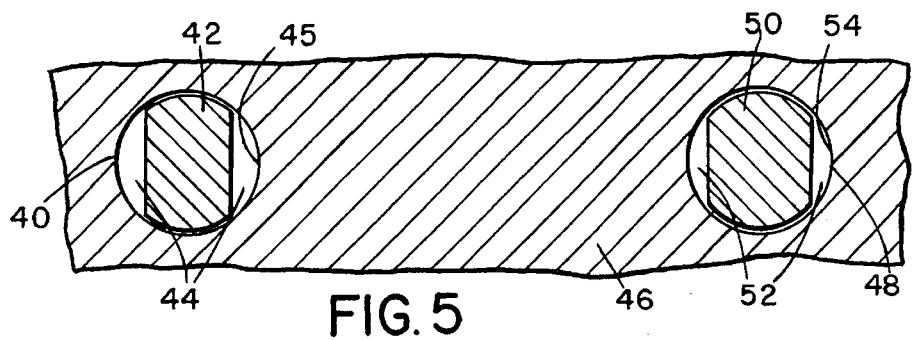
FIG. 5 is a sectional view taken on line 5—5 of FIG. 4 and extended to include both valves.

A first piston 38 is slidably mounted in chamber 32, and has a central opening 40 connecting chamber 32 to mixing chamber 36. A poppet valve member 42 is slidably mounted in chamber 32 in alignment with opening 40, and forms a variable flow area orifice 44 between the surface of valve member 42 and the peripheral rim 45 of opening 40. Similarly, a second piston 46 is slidably mounted in chamber 34, and has a central opening 48 communicating with mixing chamber 36. A second poppet valve member 50 is slidably mounted in chamber 34 in alignment with opening 48 and forms a variable flow area orifice 52 between the surface of valve member 50 and the peripheral rim 54 of opening 48, as best illustrated in FIGS. 4 and 5. Each of the poppet valve members 42 and 50 are of identical shape, and are preferably generally cylindrical valve rods of diameter equivalent to the diameters of openings 42 and 50, each having two diametrically-opposed, upwardly curved and inwardly tapering flow control surfaces 55, 56, respectively adjacent their upper end which provide precise control of the size of the respective orifices 44,52, as will be explained in more detail below. Each flow control surface is of generally parabolic shape and defines a geometrical progression with the rim of the respective piston opening as the piston and poppet move relative to one another. A reduced thickness, upper end portion 57,58 of each valve member 42,50 is provided for calibration adjustment purposes.

Figure 3:
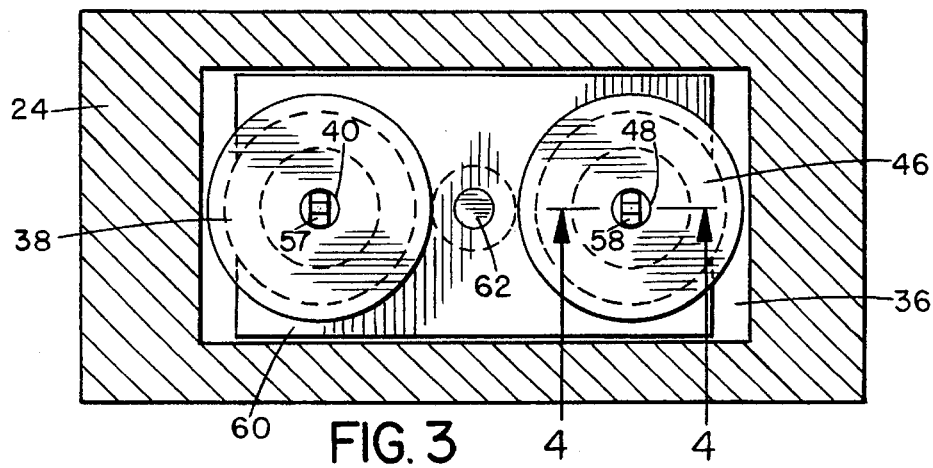
FIG. 3 is a sectional view taken on line 3—3 of FIG. 2.

The position of each valve member relative to the opening in the respective piston will control the flow area, and thus the proportions of the two gases flowing from the respective chambers into mixing chamber. The two pistons 38,46 are tied together via diaphragm or plate 60 forming the lower end wall of chamber 36, as best illustrated in FIGS. 2 and 3. Plate 60 is biased towards the lower end of chamber 36 by spring 61. A guide rod 62 extends downwardly from the center of plate 60 into guide bore 63 between the two chambers 32,34. With this arrangement, the two valve seats formed by the openings in pistons 38 and 46 are linked together and will move in response to variations in the pressure drop across the two pistons as a result of changes in the gas flow rate.

The positions of the two poppet valve members are controlled by rotating the control knob 30, which is linked to cam shaft 64 which is rotatably supported in a lower chamber 65 of the housing. Each poppet valve or rod has a lower end 66,67, respectively, which projects into the lower chamber 65 and is biased against a respective one of the cam members 68,69 mounted on cam shaft 64 beneath the respective chambers 32 and 34. The respective poppet valves are biassed against the respective cam members in any appropriate manner, for example as described below in connection with FIG. 23.

As the cam shaft rotates, the two cam members also rotate to push up or lower the respective poppet valves and thus change the respective flow areas. The arrangement is such that the proportions of air and oxygen may be varied between 21% oxygen (i.e. no oxygen flow added to the air), and 100% oxygen, 0% air. Cam member 68 therefore moves poppet valve member 42 between a closed position in which the opening 40 is closed and a maximum opening position corresponding to 100% air, while cam member 69 moves poppet valve member or rod 50 between a maximum opening position corresponding to 100% oxygen and a closed position corresponding to no added oxygen. The cams are arranged such that opening 40 is closed when opening 48 is at a maximum, and opening 48 is closed when opening 40 is at a maximum and the size of each opening decreases as the other increases. Thus, the cam members can be fixed in position to provide desired proportions of air and oxygen at the outlet. The ratio between the flow areas defined by orifices 44 and 52 will correspond to the desired blending ratio.

For low flow rates of gas through the blender, the piston diaphragm will be biassed by spring into the lowermost position illustrated in FIG. 2. However, as the gas flow rate increases, the pistons will be pushed up and the orifice sizes will increase. The control surfaces 55 and 56 on each poppet valve are shaped such that the ratio between the orifice sizes, once set by control knob 30, will remain the same regardless of the position of pistons 38 and 46. Thus, the same mixing proportions are maintained regardless of flow rate, and the same mixing valve can be used for low flow rates and high flow rates while maintaining the desired blending accuracy.

Figure 6:
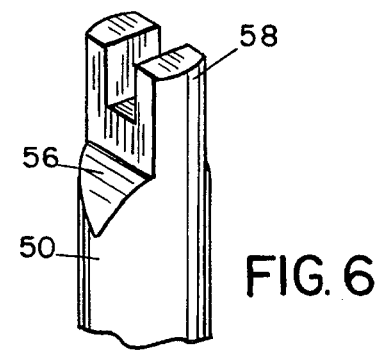
FIG. 6 is a perspective view of a typical end of a valve poppet.

As discussed above, each of the orifice control surfaces 55,56 on the respective poppet valve is precisely shaped to form a generally parabolic surface in an axial direction of gradually tapering width in a circumferential direction, as illustrated in FIGS. 4 and 6. The surface dimensions are designed such that the flow area for each incremental movement of the piston plate will correspond to a successive term of a geometrical progression. A geometrical progression is a series of terms in which each term is derived by multiplying the preceding term by a constant multiplier called the ratio of the progression. Assuming that the progression has a first term a corresponding to a minimum valve orifice and a last term 1 corresponding to a maximum valve orifice, the number of terms in the progression is n and the progression ratio is r, the general formula for the progression is:

$$1 a r^{(n-1)} \quad (1)$$

In one particular example, the total poppet travel, or piston travel relative to the poppets, was 0.075". In order to provide a progression of 60 terms with a first term a of 0.00006047 sq. in. and a last term 1 of 0.0006047 sq. in., a progression ratio of 1.0397984 is used in equation (1) above. Using this relationship, an orifice area for each increment of poppet travel, i.e. each 0.0125" of travel, can be calculated. Once all the values are calculated, a suitable shape for the poppet valve can be devised in order to produce the desired progression.

Figure 22:
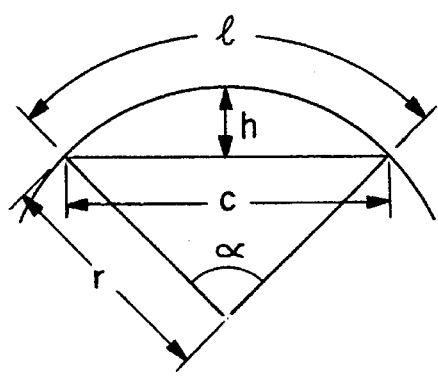
FIG. 22 is a schematic representation of a circular segment orifice as produced by a poppet control surface of the shape illustrated in FIG. 6 or 7.

One suitable orifice shape which will produce a geometrical progression is a circular segment, as illustrated in FIG. 5. This orifice shape has the advantage that a large change of radius produces a relatively small change in segment area. This makes it easier to machine the poppet surfaces with sufficient accuracy to produce the desired geometric progression. In the embodiment illustrated in FIGS. 4–6, each flow orifice corresponds to the total area of the two circular segments on each side of the poppet, as illustrated in FIG. 5. Referring to FIG. 22, the area A of each circular segment between the poppet surface and rim of the opening may be derived from the following equation:

$$A = \tfrac{1}{2}[r_1 l_1 - c(r_1 - h)] \quad (2)$$

where $r_1$ is the radius of the opening, $l_1$ is the arc length, c is the chord length, and h is the height of the segment. This area is not exactly correct for determining the flow area because the flow area must be measured normal to the flow path, as illustrated in FIG. 4, but it is a relatively good approximation. Using equations (1) and (2), successive circular segment orifice areas conforming to a geometric progression may be calculated, and the surface dimensions for producing the series of orifice areas can then be calculated. In this manner, poppets may be machined with control surfaces according to the calculated dimensions. At this point, each poppet valve is experimentally tested to determine flow rate at a series of successive positions. Since flow rate will be proportional to orifice area, any deviation of flow rate from the progression is noted, and the surface may be adjusted to provide the correct flow.

Thus, the opposing control surfaces 55 and 56 on opposite sides of each poppet each define flow areas of circular segment shape with the rim of the respective piston opening, such that the total flow area defined by each poppet increases with incremental separation between the poppet and piston according to the same geometrical progression. Once the control knob has been set to define a predetermined blending ratio with the pistons in the lowermost position, the ratio between the area of the two orifices will be the same as the selected blending ratio. If the pistons move away from the poppets, the same blending ratio will be maintained since the proportional increase in size of each orifice will be the same, as controlled by the geometrical progression ratio. Thus, for example, assume that the flow area of orifice 44 is $A_1$ and the flow area of orifice 52 is $A_2$, and the progression ratio is r, then the mixing ratio will be $A_2/A_1$. If the piston moves by one increment from a first position, then the new area of each opening will be equal to the area multiplied by the progression ratio r. In other words, $A'_1 = rA_1$ and $A'_2 = rA_2$. The ratio between the two flow areas at the new position is then:

$$\frac{A_2'}{A_1'} = \frac{rA_2}{rA_1} = \frac{A_2}{A_1} \quad (3)$$

Thus it can be seen that the same blending ratio can be maintained accurately as the pistons move to compensate for changes in flow rate.

Figure 7:
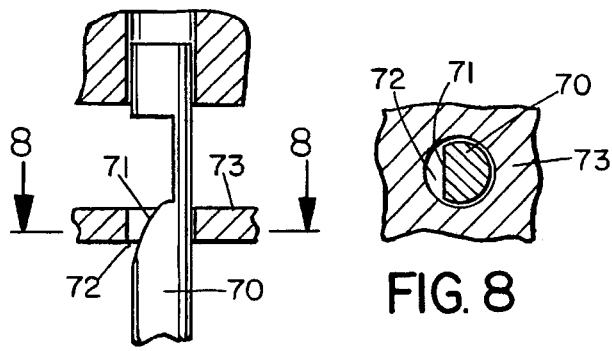
FIG. 7 is a view similar to FIG. 4, showing an alternative single wedge poppet configuration.
Figure 8:
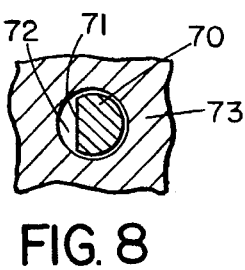
FIG. 8 is a sectional view taken on line 8—8 of FIG. 7.

Other shapes of control surfaces may be provided on the two poppet valves or in the piston openings in order to produce a flow area corresponding to a geometrical progression. FIGS. 7–20 illustrate some other examples of valve configurations for providing a geometrical progression. FIGS. 7 and 8 illustrate a first alternative valve configuration in which poppet valve member 70 has a single tapered wedge surface 71 on one side, rather than two opposing wedge surfaces 55,56 as in the first embodiment. In this case, each orifice comprises a single circular segment orifice 72 formed between the rim of the opening in piston 73 and the opposing surface 71 of the valve member, rather than two circular segments. Again, a series of opening areas may be calculated to provide the dimensions for appropriate machining of control surface 71. Each poppet valve will be provided with an identical control surface.

FIGS. 9 and 10 illustrate another alternative poppet valve 74 which has a conical control surface 75 forming an annular flow orifice 76 of varying area between the rim of a circular opening in piston 73 and the surface of the valve member. Again, the dimensions of control surface 75 for producing an orifice area which varies according to a geometrical progression may be suitably calculated.

FIGS. 11 and 12 illustrate another alternative poppet valve 77 which has an indentation or depression 78 of triangular cross-section and gradually increasing depth along curved inner end 79. This forms a triangular area orifice 80 between depression 78 and the rim of the opening in piston 73. The dimensions of this orifice required to form an area which increases incrementally according to a desired geometric progression may be readily calculated.

In the previous embodiments, the poppet valve was provided with a control surface for forming a flow orifice having the desired variation in area to produce a geometrical progression. However, the opening or through bore in each piston which forms the valve seat may alternatively be provided with an appropriately shaped and dimensioned control surface. FIGS. 13 and 14 illustrate one such arrangement, in which piston 81 has a through bore 82 into which cylindrical poppet valve 83 extends. One side of through bore 82 is provided with a generally wedge-like surface 84 corresponding substantially in shape and curvature to the surface 71 provided on the poppet valve in FIGS. 7 and 8. This provides a crescent-shaped orifice 85, and surface 84 can be shaped and dimensioned such that orifice 85 varies according to a desired geometrical progression.

FIGS. 15 and 16 illustrate a modified valve seat or piston through bore 86 which has opposing, wedge-like control surfaces 87 for controlling flow area. In this arrangement, two crescent-shaped orifices 88 are provided on opposite sides of poppet valve 83.

In the embodiment of FIGS. 17 and 18, piston 89 has a through bore 90 of conically tapering shape, equivalent to the conically shaped poppet of FIGS. 9 and 10. Poppet valve 83 is identical to the previous embodiment and defines with the piston through bore an annular flow orifice 91 with an area which will vary due to the conically tapering surface of bore 90. Again, the shape and dimensions of the conically tapering surface will be designed according to the desired geometrical progression.

FIGS. 19 and 20 illustrate another alternative in which the poppet valve 83 is identical to the previous three embodiments and a piston 92 is provided with a through bore 93 having a tapering, V-shaped recess 94 of gradually increasing depth, corresponding to the control surface provided in FIGS. 11 and 12 on the poppet valve. The V-shaped recess 94 forms a triangular shape flow orifice 95 with poppet valve 83, and the taper and dimensions of the V-shaped recess are designed such that the area will vary according to the desired progression.

These are just some examples of possible control surface shapes for producing a flow orifice of area which varies according to a geometrical progression. Any suitable surface for providing an area which varies in this way may be provided either on the poppet valve or on the piston through bore. In each case the curvature of the tapering surface is preferably of parabolic shape, since this produces a flow area which changes by a relatively large amount over a relatively short distance of movement of the poppet valve or piston.

Figure 21:
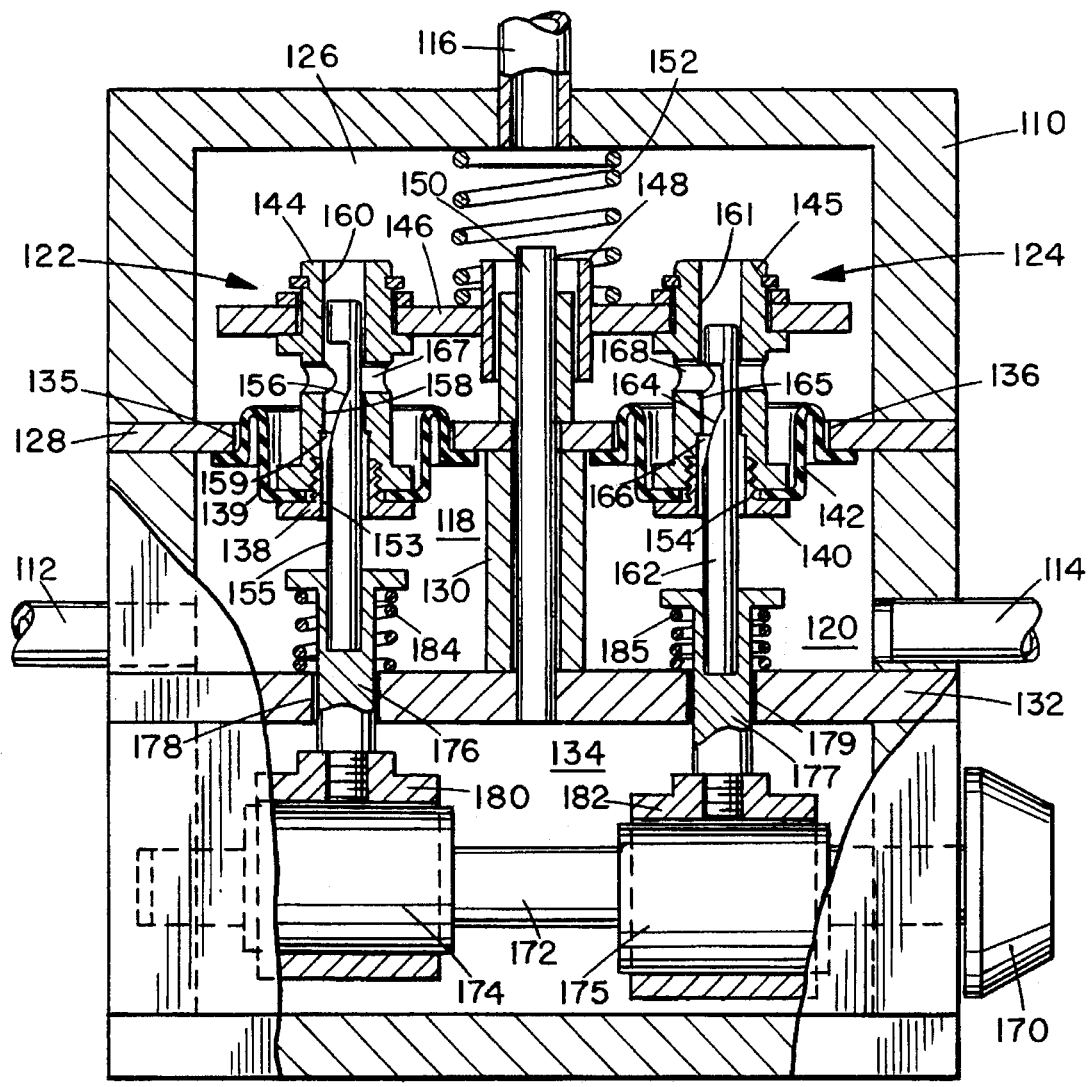
FIG. 21 is a side elevation view, partially cut away, of a mixing valve according to another embodiment of the invention.

FIG. 21 illustrates a mixing valve assembly according to another embodiment of the invention. In this embodiment, valve housing 110 has an air inlet 112, an oxygen inlet 114, and a blended gas outlet 116. The air inlet 112 is connected to an air chamber 118 and the oxygen inlet is connected to oxygen chamber 120. Control valves 122,124 respectively, control the connection of the air and oxygen chambers to a mixing chamber 126 which in turn is connected to the blended gas outlet 116. The two inlet chambers are separated from the mixing chamber by dividing wall 128, and are separated from each other by baffle 130. A lower wall 132 separates the two inlet chambers from cam chamber 134.

Dividing wall 128 has a pair of openings 135,136 above the respective inlet chambers 118 and 120, in which the respective control valves are mounted. Control valve 122 includes a first piston 138 mounted in opening 135 via rolling diaphragm 139, while control valve 124 includes a second piston 140 mounted in opening 136 via rolling diaphragm 142. Piston 138 is secured to a first valve seat member 144 extending upwardly into mixing chamber 126, while piston 140 is secured to a second valve seat member 145 extending upwardly into the mixing chamber. The two valve seat members are tied together at their upper ends by means of tie plate 146. Tie plate 146 has a central sleeve 148 slidably mounted over centering rod 150 which projects upwardly from lower wall 132 through baffle 130 and into the mixing chamber. Biassing spring 152 biases the tie plate and attached seat members and pistons in a downwards direction.

Piston 138 and valve seat member 144 have aligned through bores 153,154, respectively, and a first poppet valve member 155 projects upwardly through bore 153 and into bore 154. Popper valve member 155 comprises a cylindrical rod having a shaped, flow control surface 156. The rod diameter is less than the diameter of bore 153. Bore 154 has a step in diameter forming a reduced diameter portion 158 of diameter close to the diameter of valve member 155. The rim of the step forms a flow control orifice 159 with the opposing portion of flow control surface 156 of the valve member.

Similarly, piston 140 and valve seat member 145 have aligned through bores 160,161, respectively, and a second poppet valve member 162 projects upwardly through bore 160 and into bore 161. Poppet valve member 162 comprises a cylindrical rod having a shaped, flow control surface 164 identical to flow control surface 156 of the first poppet valve member. The rod diameter is less than the diameter of bore 160. Bore 161 has a step in diameter forming a reduced diameter portion 165 of diameter close to the diameter of valve member 162. The rim of the step forms a flow control orifice 166 with the opposing portion of flow control surface 164 of the valve member. Each valve seat member has a transverse through bore 167,168, respectively, extending across the diameter of the seat member and intersecting the axial through bore 154,161, respectively. Bores 167,168 connect the flow control orifice 159,166 to the mixing chamber. The upper end of each poppet valve member extends into the upper end portion of the valve seat member through bore for centering purposes.

As in the first embodiment, a control knob 170 on the front of the housing is linked to a cam shaft 172 extending through cam chamber 134 and rotatably mounted in the opposite end wall of the chamber to knob 170. A pair of eccentric cam members 174,175 are mounted on the cam shaft 172 in alignment with the respective poppet valve members, and are positioned to provide the desired range of mixing proportions from 100% oxygen down to 21% oxygen (100% air). The lower end of each poppet valve rod is secured in a respective plunger 176,177 which extends slidably through an opening 178,179, respectively, in lower wall 132. Each plunger 176,177 is threadably secured to a respective yoke or sleeve member 180,182, encircling the respective cam members 174,175. Each cam member is rotatable in the respective yoke, so that rotation of the cam shaft will act to pull the respective plungers and attached poppet valve members up and down. Springs 184,185 bias the yokes 180,182 against the cam surfaces at all times.

The control surfaces 156,164 in this embodiment are preferably identical to the control surface 71 of FIGS. 7 and 8 above, and are of generally parabolic shape in an axial direction, with a gradually tapering width to define a wedge-like, parabolically curved surface. This will form a circular segment flow orifice of area dependent on the position of the poppet valve relative to the orifice 159,166, respectively. Control knob 170 is rotated to provide a desired blending ratio of air to oxygen. As one gas orifice is reduced in size a set amount, the other orifice is increased by the same amount. The full counter-clockwise position of the control knob corresponds to 21% oxygen, in other words the oxygen passageway is completely shut off at this position and air flow only is permitted to the blender outlet. If the control knob is turned to the fully clockwise position, corresponding to 100% oxygen, the air orifice will be completely closed and oxygen only will flow to the blender outlet. Between these two extremes, various settings are provided which correspond to various proportions of air and oxygen in the mixture.

During operation of the mixing valve, pistons 138,140 will move together in response to change in flow rate. Since the incremental movement of each piston and orifice will be the same, the preset ratio between the flow areas of the two orifices will remain the same regardless of any piston movement, due to the fact that each flow control surface is designed to correspond to a geometrical progression, as explained above in connection with FIGS. 1–6.

The spring 152 will create a pressure drop across the control valves. At low flow rates, the pistons will be biassed downwardly by the spring into the lowermost position which is illustrated in FIG. 21. If successive areas of the flow control orifice at incremental positions correspond to a geometrical progression with a ratio R, the desired orifice area ratio is R1, and the area of the first flow control orifice is A, then the area of the second flow control orifice at the lowermost position of the orifice will be controlled by the cam position to be R1xA. Assuming that the flow rate is increased such that the pistons move up by one increment, then the new area of the first orifice will be RxA and the area of the second orifice will be RxR1xA. Thus, the orifice area ratio will remain constant. The same area ratio will be maintained substantially constantly regardless of piston movement.

The position of the pistons will be dependent on the pressure drop. If the flow is low, the pressure applied due to the spring force of spring 152 will be greater than the pressure drop, and the pistons will be held down. If the flow rate increases, the pistons will rise up until the pressure drop across the pistons times the effective area of each piston equals the spring force, unrolling the rolling diaphragms as they move upwards.

Table 1 gives one specific example of a set of orifice areas corresponding to a geometric progression having a progression ratio of 1.0397984, for an oxygen percentage in the range from 28% to 93%, and with flow control surfaces as described above in connection with FIGS. 1–6. In Table 1, poppet travel is in inches and poppet area in square inches.

TABLE 1

| AIR POPPET TRAVEL | AIR POPPET AREA | O$_2$ POPPET TRAVEL | O$_2$ POPPET AREA | RATIO | % OXYGEN |
|---|---|---|---|---|---|
| .0750000 | .0006047 | .0012500 | .0000605 | 10.00051 | 28 |
| .0737500 | .0005816 | .0025000 | .0000628 | 9.260906 | 29 |
| .0725000 | .0005593 | .00375 | .0000654 | 8.554653 | 29 |
| .0712500 | .0005379 | .0050000 | .0000680 | 7.912325 | 30 |
| .0700000 | .0005173 | .0062500 | .0000707 | 7.318228 | 30 |
| .0687500 | .0004975 | .0075000 | .0000735 | 6.768736 | 31 |
| .0675000 | .0004785 | .0087500 | .0000764 | 6.260505 | 32 |
| .0662500 | .0004602 | .0100000 | .0000795 | 5.790433 | 33 |
| .0650000 | .0004426 | .0112500 | .0000826 | 5.355656 | 33 |
| .0637500 | .0004256 | .0125000 | .0000859 | 4.953528 | 34 |
| .0625000 | .0004093 | .0137500 | .0000893 | 4.581591 | 35 |
| .0612500 | .0003937 | .0150000 | .0000929 | 4.237580 | 36 |
| .0600000 | .0003786 | .0162500 | .0000966 | 3.919400 | 37 |
| .0587500 | .0003641 | .0175000 | .0001004 | 3.625113 | 38 |
| .0575000 | .0003502 | .0187500 | .0001044 | 3.352921 | 39 |
| .0562500 | .0003368 | .0200000 | .0001086 | 3.101166 | 40 |
| .0550000 | .0003239 | .0212500 | .0001129 | 2.868314 | 41 |
| .0537500 | .0003115 | .0225000 | .0001174 | 2.652947 | 43 |
| .0525000 | .0002996 | .0237500 | .0001221 | 2.453749 | 44 |
| .0512500 | .0002881 | .0250000 | .0001269 | 2.269509 | 45 |
| .0500000 | .0002771 | .0262500 | .0001320 | 2.099102 | 46 |
| .0487500 | .0002665 | .0275000 | .0001372 | 1.941490 | 48 |
| .0475000 | .0002563 | .0287500 | .0001427 | 1.795713 | 49 |
| .0462500 | .0002465 | .0300000 | .0001484 | 1.660882 | 51 |
| .0450000 | .0002370 | .0312500 | .0001543 | 1.536174 | 52 |
| .0437500 | .0002279 | .0325000 | .0001604 | 1.420830 | 54 |
| .0425000 | .0002192 | .0337500 | .0001668 | 1.314147 | 55 |
| .0412500 | .0002108 | .0350000 | .0001735 | 1.215474 | 57 |
| .0400000 | .0002028 | .0362500 | .0001804 | 1.124210 | 58 |
| .0387500 | .0001950 | .0375000 | .0001875 | 1.039798 | 60 |
| .0375000 | .0001875 | .0387500 | .0001950 | .9617254 | 61 |
| .0362500 | .0001804 | .0400000 | .0002028 | .8895133 | 63 |
| .0350000 | .0001735 | .0412500 | .0002108 | .8227244 | 64 |
| .0337500 | .0001668 | .0425000 | .0002192 | .7609500 | 66 |
| .0325000 | .0001604 | .0437500 | .0002279 | .7038140 | 67 |
| .0312500 | .0001543 | .0450000 | .0002370 | .6509679 | 69 |
| .0300000 | .0001484 | .0462500 | .0002465 | .6020899 | 70 |
| .0287500 | .0001427 | .0475000 | .0002563 | .5568818 | 72 |
| .0275000 | .0001372 | .0487500 | .0002665 | .5150684 | 73 |
| .0262500 | .0001320 | .0500000 | .0002771 | .4763942 | 75 |
| .0250000 | .0001269 | .0512500 | .0002881 | .4406238 | 76 |
| .0237500 | .0001221 | .0525000 | .0002996 | .4075396 | 77 |
| .0225000 | .0001174 | .0537500 | .0003115 | .3769393 | 78 |
| .0212500 | .0001129 | .0550000 | .0003239 | .3486368 | 80 |
| .0200000 | .0001086 | .0562500 | .0003368 | .3224593 | 81 |
| .0187500 | .0001044 | .0575000 | .0003502 | .2982474 | 82 |
| .0175000 | .0001004 | .0587500 | .0003641 | .2758534 | 83 |
| .0162500 | .0000966 | .0600000 | .0003786 | .2551411 | 84 |
| .0150000 | .0000929 | .0612500 | .0003937 | .2359837 | 85 |
| .0137500 | .0000893 | .0625000 | .0004093 | .2182648 | 86 |
| .0125000 | .0000859 | .0637500 | .0004256 | .2018763 | 87 |
| .0112500 | .0000826 | .0650000 | .0004426 | .1867185 | 88 |
| .0100000 | .0000795 | .0662500 | .0004602 | .1726987 | 88 |
| .0087500 | .0000764 | .0675000 | .0004785 | .1597315 | 89 |
| .0075000 | .0000735 | .0687500 | .0004975 | .1477381 | 90 |
| .0062500 | .0000707 | .0700000 | .0005173 | .1366451 | 91 |
| .0050000 | .0000680 | .0712500 | .0005379 | .1263851 | 91 |
| .00375 | .0000654 | .0725000 | .0005593 | .1168954 | 92 |
| .0025000 | .0000628 | .0737500 | .0005816 | .1079808 | 92 |
| .0012500 | .0000605 | .0750000 | .0006047 | .0999949 | 93 |

With the above arrangement, compensation for increasing and decreasing gas flow rate can be made automatically without changing the gas mixing proportions. The geometrical progression of the air and oxygen control orifices allows a single blender to act as a combined low and high flow rate blender. In the past, separate high and low flow blenders have been required, with different orifice sizes. For low flow rate, a high pressure drop is needed for proper operation. A small orifice setting will provide an adequate pressure drop for proper operation of a mixing valve at low flow rates.

However, the same orifice setting will not provide a sufficient pressure drop at higher flow rates. Thus, a separate mixing valve with higher orifice settings is typically needed for high flow rate applications. This invention permits the same mixing valve to be used for all flow rates, and automatically compensates for changing flow rate by increasing the orifice sizes while maintaining the same area ratio as required for the selected mixing ratio.

Although some preferred embodiments of the invention have been described above by way of example only, it will be understood by those skilled in the field that modifications may be made to the disclosed embodiments without departing from the scope of the invention, which is defined by the appended claims.

I claim:

1. A gas mixing apparatus, comprising:

a first chamber having an inlet for connection to a supply of a first gas:

a second chamber having an inlet for connection to a supply of a second gas;

a third, mixing chamber having an outlet for a mixture of said first and second gases;

the first and second chambers having first and second passageways, respectively, connecting said first and second chambers, respectively, to said third chamber;

a first piston slidably mounted in said first passageway and having a first opening defining a first valve seat;

a first valve member movably mounted in said first chamber for movement between a closed position seated against said first valve seat to close said opening and prevent gas flow between said first chamber and said mixing chamber, and a second position defining a maximum flow area orifice between said valve member and valve seat;

a second piston slidably mounted in said second passageway and having a second opening defining a second valve seat;

a second valve member movably mounted in said second chamber for movement between a closed position seated against said second valve seat to close said opening and prevent gas flow between said second chamber and said mixing chamber, and a second position defining a maximum flow area orifice between said valve member and valve seat;

an adjustment mechanism linked to said first and second valve members to control the position of each valve member, whereby the areas of the orifices between each valve member and valve seat are controlled to select the proportions of the two gases supplied to the mixing chamber;

the first and second pistons being connected together and being movable relative to said valve seats to vary the flow area of each orifice in response to variations in pressure drop across the respective pistons; and each valve member and valve seat having opposing surfaces of predetermined shape for forming a series of orifices of progressively increasing area as said valve members and valve seats move relative to one another from said closed position to said maximum flow area position, each series corresponding to the same geometrical progression having a predetermined progression ratio.

2. The apparatus as claimed in claim 1, wherein each piston opening is circular, and each valve member comprises a generally cylindrical rod of predetermined diameter to provide a close sliding fit through the respective opening, each valve member having at least one tapering control surface of predetermined dimensions for producing said series of orifices of areas corresponding to said geometric progression.

3. The apparatus as claimed in claim 2, wherein the control surface is of parabolic curvature in an axial direction, and of gradually tapering width from said maximum opening position to said closed position, to define an orifice of circular segment shape between said valve member and opening.

4. The apparatus as claimed in claim 2, wherein each valve member has two, oppositely directed control surfaces of identical shape.

5. The apparatus as claimed in claim 2, wherein each control surface comprises a V-shaped recess of gradually increasing depth to define a generally triangular shape orifice between said recess and opening.

6. The apparatus as claimed in claim 2, wherein the control surface comprises a conical surface defining an annular orifice of varying area between the opening and valve member.

7. The apparatus as claimed in claim 1, wherein each piston opening comprises a cylindrical through bore and each valve member comprises a generally cylindrical rod of predetermined diameter to provide a close sliding fit through the respective opening, each through bore having at least one tapering control surface of predetermined dimensions for producing said series of orifices of areas corresponding to said geometric progression.

8. The apparatus as claimed in claim 1, wherein each flow control orifice is of circular segment shape.

9. The apparatus as claimed in claim 1, wherein each flow control orifice comprises two flow areas of circular segment shape on opposite sides of the valve member.

10. The apparatus as claimed in claim 1, wherein each flow control orifice is crescent-shaped.

11. The apparatus as claimed in claim 1, wherein each flow control orifice is of annular shape.

12. The apparatus as claimed in claim 1, wherein each flow control orifice is of generally triangular shape.

13. The apparatus as claimed in claim 1, including biassing means for biassing said first and second pistons into a first position when the pressure drop across the pistons is below a predetermined value, the pistons moving away from said first position to increase the flow orifice size when the pressure drop rises above said predetermined value.

14. The apparatus as claimed in claim 1, wherein said adjustment mechanism comprises a cam shaft rotatably mounted in said housing, a first cam member mounted on said shaft in alignment with said first valve member, a second cam member mounted on said shaft in alignment with said second valve member, a first cam follower having a first end biassed against the surface of said first cam member and a second end secured to said first valve member, a second cam follower having a first end biassed against the surface of said second cam member and a second end secured to said second valve member, whereby rotation of said cam shaft will move said first and second valve members back and forth in an axial direction to control the ratio between the two flow orifices.

* * * * *